United States Patent [19]

Martin et al.

[11] Patent Number: 4,822,405

[45] Date of Patent: Apr. 18, 1989

[54] HERBICIDAL OIL IN WATER COMBINATION COMPOSITIONS OF IMIDAZOLINONE HERBICIDES

[75] Inventors: Craig A. Martin, Pennington; Jerry L. Johnson, Lawrenceville, both of N.J.

[73] Assignee: American Cyanamid Company, Stamford, Conn.

[21] Appl. No.: 7,068

[22] Filed: Jan. 27, 1987

[51] Int. Cl.$^4$ .................. A01N 43/50; A01N 33/06
[52] U.S. Cl. .................................. 71/92; 71/121; 71/DIG. 1
[58] Field of Search .............. 71/92, 121, DIG. 1

[56] References Cited

U.S. PATENT DOCUMENTS

| | | | |
|---|---|---|---|
| 2,726,150 | 12/1955 | Wolter | 71/DIG. 1 |
| 3,067,254 | 12/1962 | Wilder | 71/121 |
| 4,077,795 | 3/1978 | Cooke et al. | 71/121 |
| 4,165,231 | 8/1979 | Lutz et al. | 71/121 |
| 4,174,960 | 11/1979 | Hendriksen | 71/121 |
| 4,440,562 | 4/1984 | Prill | 71/86 |
| 4,488,896 | 12/1984 | Lamb et al. | 71/92 |
| 4,541,860 | 9/1985 | Civilla et al. | 71/DIG. 1 |
| 4,608,079 | 8/1986 | Los | 71/92 |

FOREIGN PATENT DOCUMENTS

| | | | |
|---|---|---|---|
| 0978766 | 12/1975 | Canada | 71/DIG. 1 |
| 2022418A | 12/1979 | United Kingdom | 71/DIG. 1 |

Primary Examiner—Glennon H. Hollrah
Assistant Examiner—Susan P. Treanor
Attorney, Agent, or Firm—Alice C. Brennan

[57] ABSTRACT

The present invention provides novel concentrated herbicidal oil in water emulsion combination compositions of imidazolinone herbicides and dinitroaniline herbicides and methods for their preparation.

10 Claims, No Drawings

HERBICIDAL OIL IN WATER COMBINATION COMPOSITIONS OF IMIDAZOLINONE HERBICIDES

BACKGROUND OF THE INVENTION

The discovery of a potent class of herbicidal compounds, known as the imidazolinone compounds, has resulted in considerable field testing of these compounds both alone and in combination with other herbicides for various uses worldwide.

Herbicidal substituted pyridine and quinoline-2-imidazolin-2-yl acids, esters and salts are disclosed in European Pat. No. 0 041 623, which also describes aqueous compositions of water soluble salts of herbicidal pyridine and quinoline-2-imidazolin-2-yl acids which may simply be dispersed in water and applied as a dilute aqueous spray to the foilage of plants or to soil containing propagating organs thereof. Herbicides such as the 2,6-dinitroanilines, are, due to their low water solubility, normally applied as aqueous emulsions that are prepared from organic based emulsifiable concentrate compositions.

Since the use of herbicidal combinations for the control of undesirable vegetation is a well established practice, it is desirable to have stable combination compositions containing water soluble herbicidal imidazolinone acids such as 2-(4-isopropyl4-methyl-5-oxo-2-imidazolin-2-yl)-3-quinolinecarboxylic acid salts and herbicidal 2,6-dinitroaniline compounds which have a low degree of water solubility such as N-(1-ethylpropyl)-2,6-dinitro3,4-xylidine, (pendimethalin), and alpha,alpha,alpha-trifluoro-2,6-dinitro-N,N-dipropyl-p-toluidine (trifluralin).

A single composition containing both of these classes of herbicides would avoid the problems of handling, measuring and mixing which is associated with the practice of preparing tank-mixtures of individual formulations prior to spraying. Pending application for U.S. letters patent Ser. No. 880,446, of J. Parsons, filed June 30, 1986 describes nonaqueous liquid concentrate compositions of salts of 2-(4-isopropyl-4-methyl-5- oxo-2-imidazolin-2-yl)-3-quinolinecarboxylic acid which are suitable for the preparation of nonaqueous combination compositions containing herbicidal dinitroaniline compounds. However, an aqueous combination composition for these classes of herbicides has not been described. Herbicidal compositions which have been described as concentrated aqueous emulsions or concentrated oil in water emulsions containing a single water insoluble herbicide in a water insoluble solvent which is emulsified in an aqueous phase and their advantages have been described in various publications.

UK Patent Application GB No. 2,115,285A describes a concentrated aqueous emulsion containing on specific weight bases one or more liquid herbicidal phenoxyalkanecarboxylic acid esters, one or more oil soluble emulsifiers, and a water soluble dispersant as aqueous emulsions. U.S. Pat. No. 4,460,406 describes concentrated oil in water emulsion formulations containing an organic solvent soluble 2-haloacetanilde or thiocarbamate herbicide having a solution point below 25° C., a hydrocarbon solvent, a non-ionic emulsifying agent having an HLB of 18 or greater, a $C_{14}$–$C_{20}$ straight chain alcohol, and water containing an agriculturally acceptable salt or urea, all according to specific concentration ranges. U.S. Pat. No. 4,174,960 describes concentrated aqueous emulsions containing one or more water insoluble herbicidal 2,6-dinitroaniline derivatives, a water immiscible solvent, an emulsifying agent and an aqueous solution containing an inorganic salt. Additionally, in the case of 2-haloacetanildes the use of this type of formulation has been extended to the development of concentrated emulsion compositions of these water-insoluble herbicides with water soluble N-phosphonomethylglycine salts as disclosed in U.S. Pat. No. 4,440,562 which describes compositions containing, according to highly specific weight ranges, the isopropylamine salt of N-phosphonomethylglycine; a surfactant therefor; 2-chloro-2',6'-diethyl-N-(methoxymethyl)acetanilide; an organophilic clay; an emulsifier selected from the group consisting of alkylaryl sulfonates, phosphate esters of nonylphenol ethoxylates and polyalkyleneglycol ethers; an organic solvent in which 2-chloro-2'6'-diethyl-N-(methoxymethyl)acetanilide herbicide is soluble, which is nonreactive to said herbicide and which is essentially water-insoluble; and the balance being made up of water.

It is an object of this invention to provide novel concentrated oil in water emulsion combination compositions of water soluble salts of herbicidal imidazolinyl acids and 2,6-dinitroaniline herbicides, and a method for their preparation.

SUMMARY OF THE INVENTION

The invention is herbicidal compositions comprising 0.5% to 10% by weight of a herbicidally effective water soluble salt of an imidazolinyl acid, 5% to 45% by weight of a herbicidally effective 2,6-dinitroaniline derivative, a water immiscible solvent for the 2,6-dinitroaniline derivative, alkylphenol polyethylene oxide condensate and ethylene oxide/propylene oxide block copolymer emulsifying agents and an anionic dispersant, and water, the emulsifying agents and dispersant being present in an amount resulting in a physically and chemically stable concentrated oil in water emulsion.

A preferred embodiment of the invention is herbicidal concentrated oil in water emulsion compositions comprising on a weight basis about 0.5% to 10% of a water soluble salt of an imidazolinyl acid represented by formula (I) below

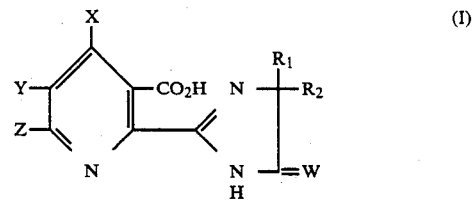

wherein
W is oxygen or sulfur; X is H, halogen, methyl or hydroxyl;
Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group or phenyl optionally substituted with one $C_1$–$C_4$ alkyl, $C_1$–$C_4$ alkoxy or halogen; difluoromethoxy, trifluoromethoxy, 1,1,2,2tetrafluoroethoxy, $C_3$–$C_8$ straight or branched alkenyloxy optionally substituted with one to three halogens, or $C_3$–$C_8$ straight or branched alkynyloxy optionally substituted with one to three halogens;

and, when taken together Y and Z may form a ring which may optionally be substituted, in which YZ or ZY are represented by —(CH$_2$)$_n$—, —(CH)$_n$—, where n is an integer of 3 or 4, or —(CH$_2$)$_2$—Q— or —(CH)$_2$—Q—, wherein Q is oxygen or sulfur, with the proviso that X is hydrogen; R$_1$ is C$_1$-C$_4$ alkyl; R$_2$ is C$_1$-C$_4$ alkyl or C$_3$-C$_6$ cycloalkyl; and when R$_1$ and R$_2$ are taken together with the carbon to which they are attached they may represent C$_3$-C$_6$ cycloalkyl optionally substituted with methyl;

5% to 45% of a herbicidal dinitroaniline derivative represented by formula (II) below

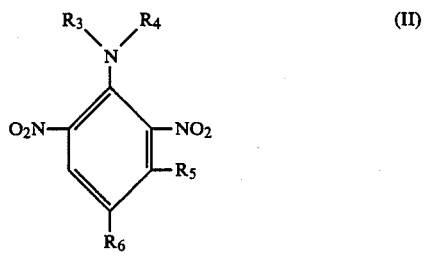

where R$_3$ is hydrogen, C$_{2-4}$ alkyl or chloroethyl, R$_4$ is C$_{2-5}$ alkyl, chloroethyl, 2-methallyl or cyclopropylmethyl, R$_5$ is hydrogen, methyl or amino and R$_6$ is trifluoromethyl, C$_{1-3}$ alkyl, —SO$_2$NH$_2$ or SO$_2$CH$_3$;

5% to 40% of a water immiscible solvent;
0.5% to 5.0% of an alkylphenol polyethylene oxide condensate;
0.5% to 5.0% of a ethylene oxide/propylene oxide block copolymer;
0% to 5.0% of an anionic dispersant; and
sufficient water to total 100%.

Surprisingly it has been found that the compositions of this invention provide physically and chemically stable concentrated oil in water emulsions of water soluble salts of herbicidal formula (I) imidazolinyl acids and formula (II) herbicidal 2,6-dinitroaniline compounds which remain homogeneous and free flowing for extended periods of time and also retain their physical stability through repeated freezing and thawing cycles without settling, separating, coalescing, or precipitating insoluble solids.

Concentrated oil in water emulsion compositions of the herbicide pendimethalin are described in copending application for U.S. letters patent Ser. No. 007,066 of C. Martin, filed 1-27-87.

The compositions of this invention comprise a continuous aqueous phase comprising a solution of a water soluble salt of a herbicidal formula (I) imidazolinyl acid having a pH in a range of from about pH 6.5 to pH 8 and preferably in a range of about pH 6.5 to pH 7.5; having dispersed therein an organic water immiscible solvent containing a herbicidal formula (II) dinitroaniline; having an average droplet size of less than 5 microns and preferably less than 2 microns; and the emulsifiers and dispersant described above.

The classes of emulsifying agents, dispersing agents and mixtures thereof which are described above have been found to be suitable for the preparation of the stable concentrated oil in water compositions containing water soluble salts of formula (I) imidazolinyl acids and the essentially water insoluble herbicidal formula (II) dinitroaniline compounds.

A preferred group of ethylene oxide/propylene oxide block copolymers for use in the compositions of this invention are butyl-omega-hydroxypoly(oxypropylene)block polymer with poly(oxyethylene) having an average molecular weight in a range of 2,400 to 3,500, with alpha-butyl-omega-hydroxy-ethylene oxide-propylene oxide block copolymers having an HLB of 12 and a viscosity at 25° C. of 2000 CPS, (TOXIMUL ® 8320, Stepan Chemical Co.) being a most preferred member of this class of emulsifiers.

Preferred alkylphenol polyethylene oxide condensates for use in the compositions of the invention are the nonylphenol ethoxylates, with nonylphenol ethoxylate (9 to 10 mols of ethylene oxide) (FLO MO ® 9N, DeSoto, Inc. Sellers Chemical Div.) being a most preferred member of this class of emulsifiers.

A preferred group of anionic dispersants are the alkali metal salts, especially the sodium salts, of fatty acid taurides or fatty acid alkyltaurides. Examples of such fatty acids, which are frequently used in the form of mixtures, are straight-chain or branched saturated or mono- or polyunsaturated aliphatic carboxylic acids having about 10 to 20 carbon atoms, such as lauric acid, palmitic acid, stearic acid, myristic acid and especially oleic acid. The alkyl radical in fatty acid alkyltaurides is a lower alkyl radical with up to 4 C atoms, especially the methyl radical, with sodium N-methyl-N-oleoyltaurate (IGEPON ® T77, GAF Corporation) being a most preferred dispersing agent.

It is of course recognized that although it is not required in order to obtain stable compositions, that the concentrated emulsion compositions of the present invention may also optionally contain minor quantities (i.e., up to 10%) of adjuvants commonly employed in agricultural emulsion formulations such as antifoaming agents, biocides, antifreezing agents, rheological control agents, coloring agents and the like, in order to accommodate cultural agricultural practices and preferences and climatic variations.

Water soluble salts of formula (I) imidazolinyl acids preferred for use in the compositions of this invention include the sodium, potassium, ammonium and organic ammonium salts of these compounds.

A preferred group of compositions of this invention include those containing a water soluble salt and preferably an ammonium salt of
2-(4-isopropyl-4-methyl-5-oxo-2-imidazolin-2-yl)nicotinic acid; or
5-ethyl-2-(4-isopropyl-4-methyl-5-oxo-2-imidazolin-2-yl)nicotinic acid; or
2-(4-isopropyl-4-methyl-5-oxo-2-imidazolin-2-yl)-5-methyl nicotinic acid; or
2-(4-isopropyl-4-methyl-5-oxo-2-imidazolin-2-yl)-3-quinolinecarboxylic acid, in the aqeuous phase;
with N-(1-ethylpropyl)-2,6-dinitro-3,4-xylidine (pendimethalin); or
alpha,alpha,alpha-trifluoro-2,6-dinitro-N,N-dipropyl-p-toluidine(trifluralin) dissolved in the dispersed organic phase.

Organic solvents suitable for use as the organic phase in the compositions of this invention include hydrocarbon, aromatic hydrocarbon, chlorinated hydrocarbon and chlorinated aromatic hydrocarbon solvents and mixtures thereof; such as toluene, xylenes, polynuclear aromatic hydrocarbons such as naphthalenes and alkyl-naphthalenes and mixtures thereof, many of which are available from the fractionation of crude oil and in general have distillation ranges in the temperature range of about 118° to 305° C. and are commercially available under a variety of tradenames; mono or polychloroalkanes such as dichloroethane, and mono or polychlorobenzene and toluenes.

The compositions of the invention may readily be prepared by high shear mixing of a mixture comprising the organic phase containing the formula (II) dinitroaniline herbicide which may also contain a portion or all of the emulsifying agent(s) with an aqueous phase containing the water soluble salt of the formula (I) acid having a pH in a range of about pH 6.5 to pH 8, which may also contain the dispersing agent, and/or a portion or all of the emulsifying agent, for a sufficient period of time to obtain an emulsion having an average droplet size of 5 microns or less and preferably less than 2 microns.

In accordance with the above procedure, compositions of the invention may be prepared by A. Prepare an aqueous phase by
1. adding the desired quantity of a formula (I) imidazolinyl acid to a sufficient quantity of water containing 1 to 1.1 molar equivalents of ammonium hydroxide;
2. adding the dispersing agent and if desired, a portion or all of the emulsifying agent;
3. agitating until a homogeneous solution results;
4. adjusting the pH of the aqueous phase to the desired range by the addition of an organic acid such as acetic acid, or additional aqueous base.

B. Prepare an organic phase by
1. adding the desired quantity of a formula (II) dinitroaniline to a sufficient quantity of the organic solvent;
2. if desired, adding a portion or all of the emulsifying agent(s);
3. agitating until all the solids dissolve;
4. optionally clarifying the organic phase by filtration.

C. Prepare the concentrated emulsion by combining the aqueous phase with the organic phase and subjecting the mixture to high shear mixing and continue mixing until a homogeneous emulsion having the desired droplet size is obtained, and package the product.

The above procedure has been found suitable for the preparation of the stable concentrated emulsions of this invention both by adding the aqueous phase to the organic phase or by adding the organic phase to the aqueous phase and has also yielded equally good results when the emulsifying agents reside in either the organic phase or the aqueous phase.

The present invention is further illustrated by the following non-limiting examples.

EXAMPLES 1-24

General Procedure

A. Prepare an aqueous phase by
1. adding the desired quantity of herbicidal imidazolinyl acid to a sufficient quantity of water containing 1 to 1.1 molar equivalents of ammonium hydroxide;
2. if desired, add the required quantity of the dispersing agent and a portion or all of the emulsifying agents, to the aqueous phase;
3. agitate until a homogeneous solution results;
4. adjust the pH of the aqueous phase to the desired range by the addition of an organic acid such as acetic acid, or additional aqueous base.

B. Prepare an organic phase by
1. adding the desired quantity of a herbicidal dinitroaniline to a sufficient quantity of the organic solvent;
2. if desired, add a portion or all of the emulsifying agent(s) to the organic phase;
3. agitating until all the solids dissolve;
4. optionally clarify the organic phase by filtration.

C. Prepare the concentrated emulsion by combining the aqueous phase and the organic phase and subjecting the mixture to a high shear mixing until a homogeneous emulsion having the desired droplet size is obtained, and collecting the thus-formed stable concentrated emulsion composition.

The above general procedure utilizing the compounds listed in Table I below yields the stable concentrated aqueous emulsion compositions listed in Table II below.

These stable compositions are obtained by employing three variations of the above general procedure:

Method 1

All the dispersing agent and emulsifying agents are added to the aqueous phase.

Method 2

The dispersing agent is added to the aqueous phase and the emulsifying agents are added to the organic phase.

Method 3

All of the emulsifying agents and the dispersing agent are added to the organic phase.

TABLE I

Herbicidal Imidazolinyl Acid
a. 2-(4-isopropyl-4-methyl-5-oxo-2-imidazolin-2-yl)-3-quinolinecarboxylic acid
b. 5-ethyl-2-(4-isopropyl-4-methyl-5-oxo-2-imidazolin-2-yl)nicotinic acid
c. 2-(4-isopropyl-4-methyl-5-oxo-2-imidazolin-2-yl)-nicotinic acid Emulsifying and Dispersing Agent
d. nonylphenol ethoxylate (9 to 10 mols of ethylene oxide)
e. alpha-butyl-omega-hydroxy-ethylene oxide propylene oxide block copolymer, HLB 12, viscosity @ 25° C.: 2000 CPS
f. sodium N—methyl-N—oleyltaurate Herbicidal Dinitroanilines
g. pendimethalin
h. trifluralin Aqueous ammonium hydroxide (29% $NH_3$)
Acetic acid
Water Organic Solvent
1. monochlorobenzene
2. xylenes
3. petroleum aromatic solvents
   3a. aromatic hydrocarbon mixture ($C_9$ to $C_{12}$ aromatics, distillation range 183–210° C.) (AROMATIC ® 150, Exxon)
   3b. aromatic hydrocarbon mixture ($C_8$ to $C_9$ aromatics, distillation range 155–173° C.) (AROMATIC ® 100, Exxon)
   3c. aromatic hydrocarbon mixture ($C_{10}$ to $C_{13}$ aromatics, distillation range 226–279° C.) (AROMATIC ® 200)
   3d. aromatic hydrocarbon mixture ($C_8$ to $C_9$ aromatics, bp 148.9° C.) (TENNECO ® T500/100)
   3e. aromatic hydrocarbon mixture (TENNECO ® T400)
   3f. hydrocarbon mixture, (distillation range 177–277° C.) (HAN ® Exxon)
   3g. aromatic hydrocarbon mixture (distillation range 210–288° C.) (PANASOL ® AN-3N, Amoco)
   3h. aromatic hydrocarbon mixture (distillation range 179–216° C.) (Shell CYCLO SOL ® 63)
   3i. aromatic hydrocarbon mixture (distillation range 160–174° C.) (Shell CYCLO SOL ® 53)
   3j. aromatic hydrocarbon mixture (distillation range 140–288° C.) (PANASOL ® AN-2L, Amoco)
   3k. aromatic hydrocarbon mixture (distillation range 177–288° C.) (PANASOL ® AN-2K, Amoco)
   3l. alkyl benzene isomer mixture (distillation TABLE I-continued range 210–305° C.) (Getty A400)

TABLE II

| | Imidazolinyl acid/ % w/w | Organic solvent/ % w/w | % Emulsifying and dispersing agent d | | e | f | Dinitro-aniline % w/w | Ammonium hydroxide % w/w | Acetic acid % w/w | Water | Method of Preparation |
|---|---|---|---|---|---|---|---|---|---|---|---|
| 1 | a/3.8 | 1/30.0 | 2.0 | 2.0 | 2.0 | g/25.0 | 0.94 | 0.03 | 34.3 | 1 |
| 2 | a/2.9 | 1/30.0 | 2.0 | 2.0 | 2.0 | g/25.0 | 0.5 | .02 | 35.6 | 1 |
| 3 | b/1.76 | 1/30.0 | 2.0 | 2.0 | 2.0 | g/30.0 | 0.35 | 0.01 | 31.88 | 1 |
| 4 | b/2.0 | 1/30.0 | 2.0 | 2.0 | 2.0 | g/34.0 | 0.4 | 0.01 | 27.59 | 1 |
| 5 | b/2.3 | 1/24.0 | 2.0 | 2.0 | 2.0 | g/40.0 | 0.46 | 0.01 | 27.23 | 1 |
| 6 | b/2.06 | 3a/28.0 | 2.0 | 2.0 | 2.0 | g/36.0 | 0.42 | 0.01 | 27.47 | 1 |
| 7 | b/2.06 | 3a/30.0 | 2.0 | 2.0 | 0.0 | g/36.0 | 0.42 | 0.01 | 27.47 | 1 |
| 8 | b/2.0 | 3a/28.0 | 2.0 | 2.0 | 2.0 | g/36.0 | 0.4 | 0.01 | 27.4 | 2 |
| 9 | a/4.6 | 1/30.4 | 2.1 | 1.9 | 2.0 | h/30.2 | 1.4 | 0.4 | 27.0 | 2 |
| 10 | a/5.3 | 3a/30.0 | 2.0 | 2.0 | 2.0 | h/31.8 | 1.2 | 0.3 | 25.4 | 2 |
| 11 | a/4.9 | 1/30.0 | 2.0 | 2.0 | 2.0 | h/31.2 | 1.3 | 0.4 | 26.1 | 2 |
| 12–22 | a/5.3 | 3b-1/30.0 | 2.0 | 2.0 | 2.0 | h/31.8 | 1.4 | 0.3 | 25.3 | 2 |
| 23 | b/1.41 | 1/33.0 | 2.0 | 2.0 | 2.0 | g/23.9 | 0.28 | 0.01 | 35.4 | 3 |
| 24 | b/1.41 | 1/16.5 and 2/16.5 | 2.0 | 2.0 | 2.0 | g/23.9 | 0.28 | 0.01 | 35.4 | 3 |

EXAMPLE 25

Low temperature stability of concentrated aqueous emulsion compositions of the invention Three 10 mL samples of compositions 1, 24 and 25 prepared in the above example and a comparative control composition containing on a weight basis 38.3% pendimethalin, 52.9% monochlorobenzene, 5.4% surfactants, are placed in a constant temperature bath maintained at 5° C. and the temperature of the samples is allowed to equilibrate for 24 hours.

The samples are visually inspected for evidence of crystallization or freezing. The temperature of the bath is then lowered in 1°–2.5° C. increments holding the sample at each temperature for 24 hours until crystallization or freezing is observed.

The thawing characteristics of each of the compositions is then determined by holding the samples at −20° C. for 24 hours, and then allowing them to stand at 7° C. in a constant temperature bath until no solids are present.

The results of these experiments are summarized in Table III below.

TABLE III

| Composition | Low temperature Freezing point/ Crystallization temp °C. | Thawing time at 7° C. hours |
|---|---|---|
| Control | −3.5 crys. | 48.0 |
| 1 | −8.0 fp | 2.5 |
| 23 | Sample does not freeze at −10 | — |
| 24 | Sample does not freeze at −10 | — |

What is claimed is:

1. Herbicidal concentrated oil in water emulsion composition comprising on a weight basis about 0.5% to 10% of a water soluble salt of an imidazolinyl acid represented by formula (I) below

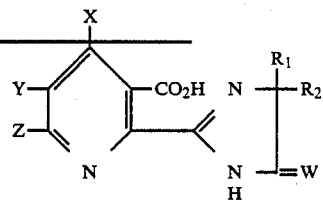

wherein
W is oxygen or sulfur; X is H, halogen, methyl or hydroxyl;
Y and Z are each hydrogen, halogen, $C_1-C_6$ alkyl, hydroxyloweralkyl, $C_1-C_6$ alkoxy, $C_1-C_4$ alkylthio, phenoxy, $C_1-C_4$ haloalkyl, nitro, cyano, $C_1-C_4$ alkylamino, diloweralkylamino or $C_1-C_4$ alkylsulfonyl group or phenyl optionally substituted with one $C_1-C_4$ alkyl, $C_1-C_4$ alkoxy or halogen; difluoromethoxy, trifluoromethoxy, 1,1,2,2-tetrafluoroethoxy, $C_3-C_8$ straight or branched alkenyloxy optionally substituted with one to three halogens, or $C_3-C_8$ straight or branched alkynyloxy optionally substituted with one to three halogens;
or, when taken together Y and Z may form a ring in which YZ or ZY are represented by —$(CH_2)_n$—, —$(CH)_n$—, where n is an integer of 3 or 4, with the proviso that X is hydrogen;
$R_1$ is $C_1-C_4$ alkyl;
$R_2$ is $C_1-C_4$ alkyl or $C_3-C_6$ cycloalkyl; and when $R_1$ and $R_2$ are taken together with the carbon to which they are attached they may represent $C_3-C_6$ cycloalkyl optionallly substituted with methyl;
5% to 45% of pendimethalin;
5% to 40% of a water immiscible solvent;
0.5% to 5.0% of an alkylphenol polyethylene oxide condensate;
0.5% to 5.0% of a ethylene oxide/propylene oxide block copolymer;
0% to 5.0% of an anionic dispersant; and sufficient water to total 100%.

2. A composition according to claim 1 comprising a continuous aqueous phase of a solution of a water soluble salt of a herbicidal formula (I) imdazolinyl acid having a pH in a range of from about pH 6.5 to pH 8; having dispersed therein an organic water immiscible solvent containing pendimethalin, having an average droplet size of less than 5 microns.

3. A composition according to claim 2 comprising an aqueous phase of a solution of a water soluble salt of
2-(4-isopropyl-4-methyl-5-oxo-2-imidazolin-2-yl)nicotinic acid; or
5-ethyl-2-(4-isopropyl-4-methyl-5-oxo-2-imidazolin-2-yl)nicotinic acid; or
2-(4-isopropyl-4-methyl-5-oxo-2-imidazolin-2-yl)-5-methyl nicotinic acid; or
2-(4-isopropyl-4-methyl-5-oxo-2-imidazolin-2-yl)-3-quinolinecarboxylic acid, in the aqueous phase;
with N-(1-ethylpropyl)-2,6-dinitro-3,4-xylidine (pendimethalin);
dissolved in the dispersed organic phase.

4. A composition according to claim 3 wherein
the alkylphenol polyethylene oxide condensate is a nonylphenol ethoxylate with 9 to 10 mols of ethylene xide;
the ethylene oxide propylene oxide block copolymer is a butyl-omega-hydroxypoly(oxypropylene)block copolymer with poly(oxyethylene) having a molecular weight in a range of 2,400 to 3,500;
the anionic dispersing agent is an alkali metal salt of fatty acid tauride or fatty acid alkyltauride.

5. A composition according to claim 4 wherein the dispersed organic phase has an average droplet size of less than 2 microns.

6. A composition according to claim 5 wherein the organic solvent is chlorobenzene, xylene or an aromatic hydrocarbon mixture having a distillation range in a temperature range of 118° C. to 305° C.

7. A composition according to claim 6 wherein the surfactants and dispersants are
alpha-butyl-omega-hydroxy-ethylene oxide-propylene oxide block copolymer having an HLB of 12 and a viscosity at 25° C. of 2,000 CPS,
nonylphenol ethoxylate (9 to 10 mols of ethylene oxide), and
sodium N-methyl-N-oleoyltaurate.

8. A composition according to claim 7 comprising
2% to 4% 2-(4-isopropyl-4-methyl-5-oxo-2-imidazolin-2-yl)-3-quinolinecarboxylic acid;
15% to 25% pendimethalin;
25% to 35% monochlorobenzene;
1.5% to 2.5% alpha-butyl-omega-hydroxy-ethylene oxide-propylene oxide block copolymer having an HLB of 12 and a viscosity at 25° C. of 2,000 CPS;
1.5% to 2.5% nonylphenol ethoxylate (9 to 10 mols of ethylene oxide);
0% to 2% sodium N-methyl-N-oleoyltaurate and sufficient water to total 100%.

9. A composition according to claim 7 comprising
30% to 40% pendimethalin;
1.5% to 4% 5-ethyl-2-(4-isopropyl-4-methyl-5-oxo-2-imidazolin-2-yl)nicotinic acid;
25% to 35% aromatic solvent;
1% to 3% alpha-butyl-omega-hydroxy-ethylene oxide-propylene oxide block copolymer having an HLB of 12 and a viscosity at 25° C. of 2,000 CPS;
1% to 3% nonylphenol ethoxylate (9 to 10 mols of ethylene oxide);
0% to 2.5% sodium N-methyl-N-oleoyltaurate and sufficient water to total 100%.

10. Herbicidal composition comprising 0.5% to 10% by weight of a herbicidally effective water soluble salt of a 2-imidazolyinyl-nicotinic acid or 2-imidazolinyl-3-quinolinecarboxylic acid, 5% to 45% by weight of pendimethalin, a water immiscible solvent for pendimethalin, alkylphenol polyethylene oxide condensate and ethylene oxide/propylene oxide block copolymer emulsifying agents and an anionic dispersant, and water, the emulsifying agents and dispersant being present in an amount resulting in a physically and chemically stable concentrated oil in water emulsion.

* * * * *